(12) United States Patent
De Coulon et al.

(10) Patent No.: US 8,784,640 B2
(45) Date of Patent: Jul. 22, 2014

(54) AMPEROMETRIC ELECTROCHEMICAL SENSOR AND METHOD FOR MANUFACTURING SAME

(75) Inventors: Yves De Coulon, Thielle-Wavre (CH); Carine Beriet, Peseux (CH); Philippe Niedermann, Peseux (CH)

(73) Assignee: Neroxis SA, Neuchatel (CH)

( * ) Notice: Subject to any disclaimer, the term of this patent is extended or adjusted under 35 U.S.C. 154(b) by 258 days.

(21) Appl. No.: 13/263,247

(22) PCT Filed: Apr. 14, 2010

(86) PCT No.: PCT/EP2010/054854
§ 371 (c)(1),
(2), (4) Date: Oct. 6, 2011

(87) PCT Pub. No.: WO2010/119045
PCT Pub. Date: Oct. 21, 2010

(65) Prior Publication Data
US 2012/0036921 A1 Feb. 16, 2012

(30) Foreign Application Priority Data
Apr. 15, 2009 (EP) ..................................... 09157979

(51) Int. Cl.
*G01N 27/49* (2006.01)
*G01N 27/404* (2006.01)
(52) U.S. Cl.
CPC .................................. *G01N 27/4045* (2013.01)
USPC ..... 205/775; 204/403.01; 204/415; 422/68.1; 422/82.01; 435/287.1
(58) Field of Classification Search
USPC ............... 204/433, 403.01–403.15, 406–419, 204/421–429; 73/61.61; 422/68.1, 82.01; 435/287.1
See application file for complete search history.

(56) References Cited

U.S. PATENT DOCUMENTS

| | | | |
|---|---|---|---|
| 5,393,399 A * | 2/1995 | Van den Berg et al. | 204/412 |
| 6,572,748 B1 * | 6/2003 | Herrmann et al. | 204/435 |
| 2008/0202944 A1 * | 8/2008 | Santoli et al. | 205/775 |

FOREIGN PATENT DOCUMENTS

EP 0 586 982 A1 3/1994

OTHER PUBLICATIONS

Van Den Berg et al. (Transducers, 2991, pp. 233-236).*
Ul Haque et al.: "A MEMS fabricated cell electrophysiology biochip for in silico calcium measurements", Sensors and Actuators B, Elsevier Sequoia S.A., Lausanne, CH, vol. 123, No. 1, Mar. 30, 2007, pp. 391-399, XP022011225, ISSN: 0925-4005, paragraphs [0002], [03.1]; figure 1.

(Continued)

*Primary Examiner* — Jennifer Dieterle
(74) *Attorney, Agent, or Firm* — Young & Thompson

(57) ABSTRACT

An amperometric electrochemical sensor with a fixed potential used in a probe for measuring the content of an oxidation reduction substance dissolved in a liquid, in particular the chlorine content. The sensor (1) includes an insulating substrate (2), a set of electrodes consisting of a working electrode (3), an auxiliary electrode (4) and a reference electrode, at least one of the working electrode (3) and auxiliary electrode (4) being configured on the insulating substrate (2). At least one of the working electrode (3) and auxiliary electrode (4) is covered with an insulating layer (8), the insulating layer (8) including at least one opening exposing at least one of the working electrode (3) and auxiliary electrode (4).

18 Claims, 5 Drawing Sheets

(56) References Cited

OTHER PUBLICATIONS

Kim H-J et al.: "A direct analysis of nanomolar metal ions in environmental water samples with Nafion-coated microelectrodes", Elecrochimica Acta, Elsevier Science Publishers, Barking, GB, vol. 50, No. 1, Nov. 15, 2004, pp. 205-210, XP004603611, ISSN: 0013-4686, Paragraphs [0002], [0003]; figure 1.

Kim P et al.: "An electrochemical interface for integrated biosensors", Proceedings of IEEE Sensors 2003. 2nd IEEE International Conference on Sensors. Toronto, Canada, Oct. 22-24, 2003; [IEEE International Conference on Sensors], New York, NY; IEEE, US, vol. conf. 2, Oct. 22, 2003, pp. 1036-1040vol. 2, XP010691066, ISBN: 978-0-7803-8133-9- pp. 1038, col. 2-p. 1039, col. 1; figure 3.

Alonso L. M.A et al.: "Biosensor based on platinum chips for glucose determination" Analytical Chimica Acta, Elsevier, Amsterdam, NL, vol. 547, No. 2, Aug. 22, 2005, pp. 209-214, CP004999141, ISSN: 0003-2670, paragraph [0002]; figure 2.

F. J. Del Campo et al.: "Improved free chlorine amperometric sensor chip for drinking water application", Analytica Chimica Acta, vol. 554, Sep. 19, 2005, pp. 98-104, XP002587694, Paragraphs [02.1], [2.2].

Neuman M. R. et al: "Batch-produced microfabricated ion-selective electrodes: reproducibility, reliability and yields", Engineering in Medicine and Biology Society, 1995, New York, NY, USA, IEEE, US, vol. 2, Sep. 20, 1995, pp. 1557-1558, XP010214855, ISBN: 978-0-7803-2475-6, p. 1557; figure 1.

Wang S-H et al.: "Development of a solid-state thick film calcium ion-selective electrode" Sensors and Actuators B, Elsevier Sequoia S.A., Lausanne, CH, vol. 96, No. 3, Dec. 1, 2003, pp. 709-716, XP004475599, ISSN: 0925-4005, paragraphs [0001], [0002]; figure 1.

European Search Report, dated Jul. 23, 2009, from corresponding European application.

International Search Report, dated Jul. 7, 2010, from corresponding PCT application.

\* cited by examiner

AMPEROMETRIC ELECTROCHEMICAL SENSOR AND METHOD FOR MANUFACTURING SAME

TECHNICAL FIELD

The present invention relates to the field of electrochemical sensors. It more particularly relates to an amperometric electrochemical sensor, with a fixed potential, used in a probe for measuring the content of an oxidation reduction substance dissolved in a liquid, in particular the chlorine content.

BACKGROUND OF THE INVENTION

The present invention relates to electrochemical sensors comprising at least one working electrode, a counter electrode and a reference electrode, for which one works at a constant potential, and in which one measures the current circulating between the working electrode and the counter electrode, caused by an oxidation reduction reaction at the working electrode. As a result, the invention does not relate to sensors based on potentiometric measurements, of the Ion-Selective Electrode type, comprising two electrodes, i.e. a working electrode and a reference electrode, between which a difference in potential is measured. Such sensors are described in the publication by UI Hague et al. A MEMS fabricated cell electrophysiology biochip for in silico calcium measurements, Sensors and Actuators B; Elsevier Sequoia S A. Lausanne, C H, vol. 123, no. 1, 2007 Mar. 30, pages 391-399, in the publication by Neuman M R et al. Batch-produced microfabricated ion-selective electrodes, Engineering in medicine and biology society, 1995, IEEE 17th Annual Conference Montreal, Vol. 2, 1995 Sep. 20, pages 1557-1558, and in the publication by Wang S-H et al, Development of a solid-state thick film calcium ion-selective electrode, Sensor and Actuators B, Elsevier Sequoia S A; Lausanne C H, vol. 96, no. 3, 2003 Dec. 1, pages 709-716. These sensors are used in the field of biomedical measurements, to measure the pH, the potassium or calcium concentration in biological fluids.

The invention also does not relate to sensors for which one measures a current, but by varying the potential over time, such as sensors using the Square Wave Anodic Stripping Voltammetry (SWASAV) technique to measure the heavy metals, described in the publication by KIM H-J et al. A direct analysis of nanomolar metal ions in environmental water samples with Nafion-coated microelectrodes, Electrochimica Acta, Elsevier Science Publisher, Barking G B, Vol. 50, no. 1, 2004 Nov. 15, pages 205-210. Such sensors containing mercury are not in compliance with environmental standards.

Amperometric sensors of the type of that of the present invention are for example described in patent EP 0 586 982. Patent EP 0 586 982 describes a first type of integrated sensor comprising an insulating substrate on which three electrodes are formed, i.e. a working electrode, a counter electrode and a reference electrode. The electrodes are then covered with a diffusion membrane, which covers all of the three electrodes.

Another type of sensor is also described and comprises an insulating substrate comprising an insulating layer, in which openings are formed. Each opening receives a metal deposition intended to form one of the electrodes. A diffusion membrane completely covers the active conducting part of the working electrode by overhanging through its entire peripheral area.

One such type of sensor requires adapting the insulating layer to each alternative embodiment of the electrodes, and therefore modifying the entire manufacturing method as a function of the desired shape of the electrodes.

Furthermore, the arrangement of the layers requires providing for a contact zone under the electrodes. Moreover, the geometric dimension of the working electrode must be sufficient, from several hundred micrometers to one millimeter, to make it possible to deposit the membrane there.

Moreover, sensors are known that are used to measure protein or glucose concentrations. These species not being electroactive, it is necessary to use a membrane in which an electroactive species is immobilized serving as intermediate species for the reaction. This additional species, used for the measurement at the working electrode, is therefore not dissolved in the medium. Such sensors are described in the publication by Kim P et al. An electrochemical interface for integrated biosensors. IEEE International Conference on sensors, New York, vol. CONF. 2, 2003 Oct. 22, pages 1036-1040 vol. 2, and in the publication by Alonso Lomillo M A et al Biosensor Based on Platinum Chips for Glucose Determination, Analytica Chimica Acta, Elsevier, Amsterdam, N L, vol. 547, no. 2, 2005 Aug. 22, pages 209-214. Unlike the amperometric sensors of the inventive type for which the reaction occurs at the working electrode, these sensors comprise a membrane that constitutes the reaction site for the undissolved electroreactive species, the sensor serving to detect the current of that reaction. Such sensors have the drawback of having a limited lifetime, as the electroreactive membrane becomes charged with species to be measured and tends to leak after a certain usage time.

One aim of the present invention is therefore to offset these drawbacks, by proposing an amperometric sensor that can be made using a simple manufacturing method and whereof only one step must be modified to manufacture electrodes having the desired shape, all of the other steps of the method being the same irrespective of the type of electrodes.

Another aim of the present invention is to propose a sensor whereof the lifetime is improved, in particular by increasing the adhesion of the polymer membrane used as diffusion membrane on a selected insulator.

Another aim of the present invention is to propose a manufacturing method making it possible to produce a nanometric insulating structure between the membrane and the electrodes.

Another aim of the present invention is to propose a sensor making it possible to directly access the electrodes to make the connections.

Another aim of the present invention is to propose a sensor making it possible to have a substrate other than a silicon substrate, and in particular a transparent substrate.

Another aim of the present invention is to propose a sensor making it possible to be miniaturized, without liquid electrolyte, and to use two same sensors in a same probe in a limited space.

BRIEF DESCRIPTION OF THE INVENTION

To that end, proposed is an amperometric electrochemical sensor with a fixed potential for measuring the content of an oxidation reduction substance dissolved in a liquid, comprising an insulating substrate, a set of electrodes made up of at least three electrodes, i.e. a working electrode, a counter electrode and a reference electrode, at least one of said working electrode and counter electrode being configured on said insulating substrate. According to the invention, at least one of said working electrode and counter electrode is covered with an insulating layer, and said insulating layer includes at least one opening exposing at least one of said working electrode and counter electrode, so that the periphery of the electrode is covered by the insulating layer.

Preferably, the working electrode and the counter electrode are both on the insulating substrate.

Preferably, the oxidation reduction substance is a disinfecting species of said liquid. Advantageously, said liquid is water and said disinfecting oxidation reduction substance is preferably chosen from among the group consisting of HOBr, HOCl, $ClO_2$, $Cl_2$, Chloramines and ozone.

According to another alternative embodiment, said oxidation reduction substance is a gas dissolved in liquid, such as oxygen.

Advantageously, said opening can have been formed by etching of the insulating layer using a mask, in particular a photolithographic mask, the configuration of which varies as a function of the desired electrode configuration.

According to the alternative embodiments, the sensor can also comprise at least one first polymer membrane deposited in said opening. Preferably, said membrane is a membrane having a selectivity to said oxidation reduction substance, and preferably having a selectivity to the disinfecting oxidation reduction substance.

Preferably, the membrane can completely cover said opening by overhanging on the insulating layer through its entire peripheral zone.

According to one alternative embodiment, the sensor can comprise a non-planar working electrode arranged in the insulating substrate, said membrane being made so that its upper surface is at the insulating substrate comprising the counter electrode.

According to the alternative embodiments, the sensor can comprise a first polymer membrane to define a diffusion layer and a second polymer membrane deposited on the first membrane to select the species to be measured.

According to the alternative embodiments, the insulating layer can comprise several openings separated by small islands of insulating material, so as to expose a set of electrode elements. The first polymer membrane can then cover all of the openings or can include several membrane elements respectively covering each opening by individually overhanging on the insulating layer through their respective peripheral zone.

Advantageously, the insulating layer can comprise homogenous nanostructured openings distributed over the surface of the electrode randomly or geometrically.

Preferably, the substrate can be made in a material chosen from among the group comprising silicon, glass, ceramics and quartz.

According to the alternative embodiments, at least one of the working electrode and counter electrode can have a shape chosen from the group of a circular, microperforated or interdigitated shape.

Advantageously, the sensor can comprise connection means for connecting the electrodes to a measuring circuit, said connection means being directly connected to the electrodes.

The present invention also relates to a method for manufacturing an amperometric electrochemical sensor, with a fixed potential, as described above, comprising an insulating substrate, a set of electrodes made up of at least three electrodes, i.e. a working electrode, a counter electrode and a reference electrode, at least one of said working electrode and counter electrode being configured on said insulating substrate, said method comprising the following steps:

depositing a layer of conductive material on said insulating substrate, etching said conductive material to define at least one of said working electrode and counter electrode, depositing a low temperature specific insulating layer on the layer of conductive material, and making at least one opening in the insulating layer exposing at least one of said working electrode and counter electrode.

Advantageously, the step for making at least one opening in the insulating layer is done by etching using a photolithographic mask whereof the configuration varies as a function of the desired electrode configuration.

This method makes it possible to modify only the last step defined above by modifying the mask used to make the opening so that it corresponds to the desired shape of the electrodes. The other steps of the method remain the same for all electrode shapes.

Preferably, the method can also comprise a step consisting of covering the insulating layer and its openings with at least one polymer membrane.

The present invention also relates to an amperometric probe for measuring the content of an oxidation reduction substance dissolved in a liquid comprising at least one sensor as defined above.

Advantageously, the probe can comprise a body containing data processing means and transmission means and a dry head, without electrolytes and detachable, in which the senor(s) are arranged for redundancy.

Advantageously, the detachable head is disposable and contains calibration information for the probe and a unique numeric identifier for the head.

Such an electrochemical measuring probe makes it possible to perform measuring operations in a pressurized fluid up to 10 bars without any maintenance and without recalibration over a period of one year.

The invention also relates to the use of a sensor as described above to measure the content of an oxidation reduction substance dissolved in a liquid, in particular a dissolved disinfecting oxidation reduction substance.

BRIEF DESCRIPTION OF THE DRAWINGS

Other features of the invention will emerge from the following description, done in reference to the appended drawings, in which.

DETAILED DESCRIPTION OF THE INVENTION

Figure 1:
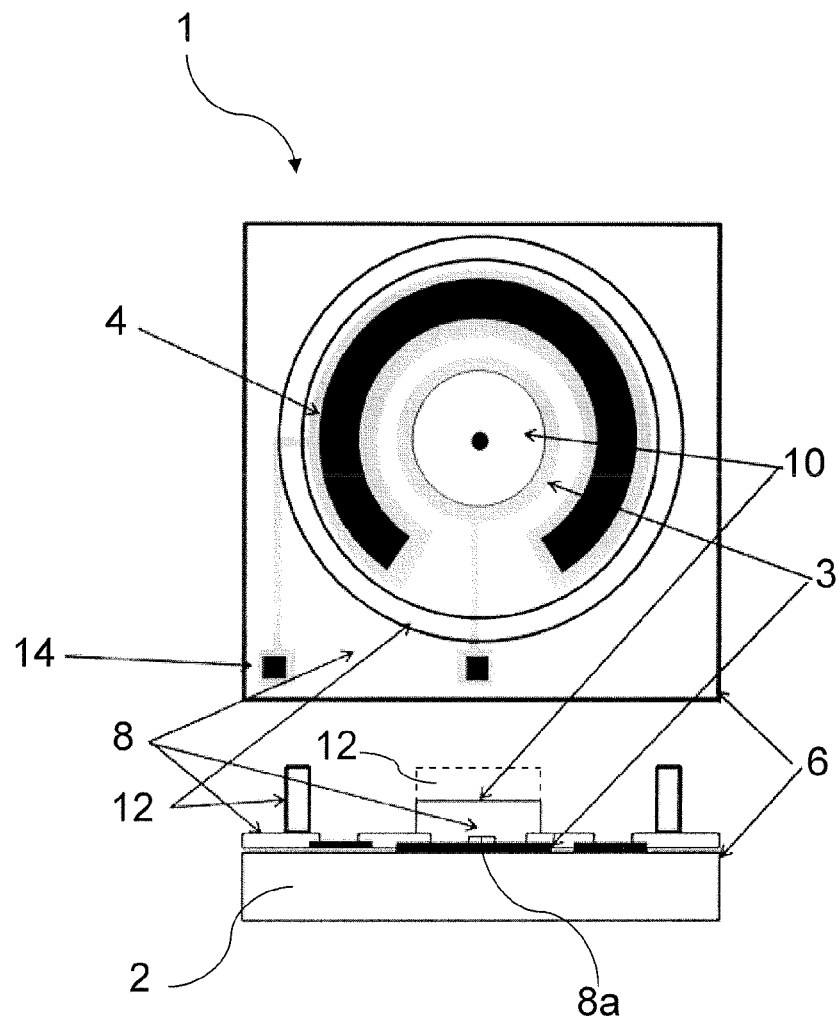
FIG. 1 is a top cross-sectional view of one alternative embodiment of a sensor according to the invention.

FIG. 1 shows an amperometric electrochemical sensor 1 intended for measuring the content of an oxidation reduction substance dissolved in a liquid, comprising an insulating substrate 2, a set of electrodes made up of a working electrode 3, a counter electrode 4 and a reference electrode (not shown), the working electrode 3 and the counter electrode 4 being configured on said insulating substrate 2. In the present description, the term "insulating substrate" designates a flat substrate, intrinsically insulating (glass, ceramic or quartz, for example), or a conductive substrate (silicon, for example) made insulating by applying a first insulating layer. When the substrate is intrinsically insulating, the first insulating layer is not necessary.

The amperometric measuring principle is based on that of a Clark cell with a working electrode, a counter electrode and a reference electrode. This amperometry principle is based on measuring the current between the working electrode and the counter electrode that is caused by an oxidation reduction reaction at the working electrode. The reference is chosen so that the current measured at the working electrode is directly proportionate to the concentration of an oxidation reduction substance dissolved in the liquid to be analyzed. This oxidation reduction substance can for example be a disinfecting species, such as chlorine in HOCl or $ClO_2$ form. The sensor also detects biochlorines, or the chlorine produced by water-salt electrolysis systems. The electric potential of the working electrode relative to the measured liquid is obtained by a separate reference electrode and is monitored by a potentiostatic electronic system.

In the illustrated examples, the substrate 2 is made from silicon, cut out, after the appropriate photolithographic treatments, from a silicon wafer traditionally in the manufacturing technique for semiconducting components. It is then covered with a first insulating layer 6, for example silicon oxide $SiO_2$, so as to obtain an insulating substrate.

The working electrode 3 and the counter electrode 4 are deposited in the form of a fine metal film on the first insulating layer 6. The electrodes can be made from platinum, gold, titanium, ruthenium or amorphous diamond.

According to the invention, the working electrode 3 and the counter electrode 4 are covered with a second insulating layer 8, preferably made from silicon nitride ($Si_3N_4$), said second insulating layer 8 comprising different openings exposing the metal to form the active surfaces of the working electrode 3 and the counter electrode 4. The periphery of the electrodes remains covered and protected by the second insulating layer 8. This second insulating layer is deposited at a low temperature so as not to harm the conductive layers making up the working electrode 3 and the counter electrode 4, which can be made from different types of metals, for example.

The openings, microscopic or nanoscopic, can be formed in the second insulating layer 8 using the traditional etching techniques by means of a photolithographic mask. This technique makes it possible to manufacture an insulating substrate having a metal film and the second insulating layer shared by all of the sensors, and to provide a photolithographic mask with a geometry adapted to the desired shape of the working electrode and the counter electrode only during the etching step of the second insulating layer.

Thus, depending on the geometry of the mask, it is possible to obtain structuring of the second insulating layer 8 so as to create square, circular, microperforated electrodes to form an array of microelectrodes with a size of several tens of micrometers, interdigitated electrodes.

For example, in reference to FIG. 1, the second insulating layer 8 is etched so as to form circular openings while leaving an element or small island 8a of insulating material at the center of the working electrode 3.

The second insulating layer 8 can also comprise nanostructured openings formed by manufacturing, on the second insulating layer 8, random nanostructures, which are then etched to form said nanostructured openings arranged randomly, but homogenously on the surface of the electrode. The nanostructures can be formed by phase separation of two non-miscible polymers by spin coating. The mean lateral size of the openings can be adjusted by manipulating the parameters of the method (nature of the polymers, speed of the spin coating and weight of the polymers).

The openings made in the second insulating layer 8 are filled with a first polymer membrane 10 that defines the diffusion layer for the oxidation or the electrochemical reduction. Preferably, the membrane 10 completely covers the openings by overhanging on the insulating layer 8 through its entire peripheral zone.

The first polymer membrane 10 is a membrane with a certain selectivity to the dissolved oxidation reduction substance to be measured.

This membrane 10 has no measurement effect and is simply a filtration membrane for the species to be measured. This species is then oxidized or reduced at the working electrode. The determination of the content of the species to be measured is therefore direct and is done directly at the working electrode.

The inventive sensor does not comprise any membrane containing an electroreactive species serving as intermediate species for the oxidation reduction reaction.

According to the alternatives, a single continuous polymer membrane can be used to cover all of the openings. According to other alternatives, the first polymer membrane is formed by several membrane elements that respectively cover each opening by individually overhanging on the different elements of the second insulating layer 8 through their entire respective peripheral zone.

Thus, the diffusion membrane 10 adheres to the metal electrodes, but also adheres to the second insulating layer 8 at the periphery of the openings and small islands of insulating material left between the openings. Furthermore the shape of the openings and the electrodes can be chosen so as to adjust the proportion of polymer membrane/insulating layer and polymer membrane/electrodes contact surface. Lastly, the material of the second insulating layer 8, such as silicon nitride or oxide, makes it possible to establish covalent bonds with the polymer membrane 10 owing to chemical surface treatments during the manufacture method.

Thus, the adhesion of the membrane 10 is greatly improved, which leads to increased performance of the sensor in terms of selectivity, stability and reliability, over a period of one year in water without recalibration or maintenance.

Figure 3:
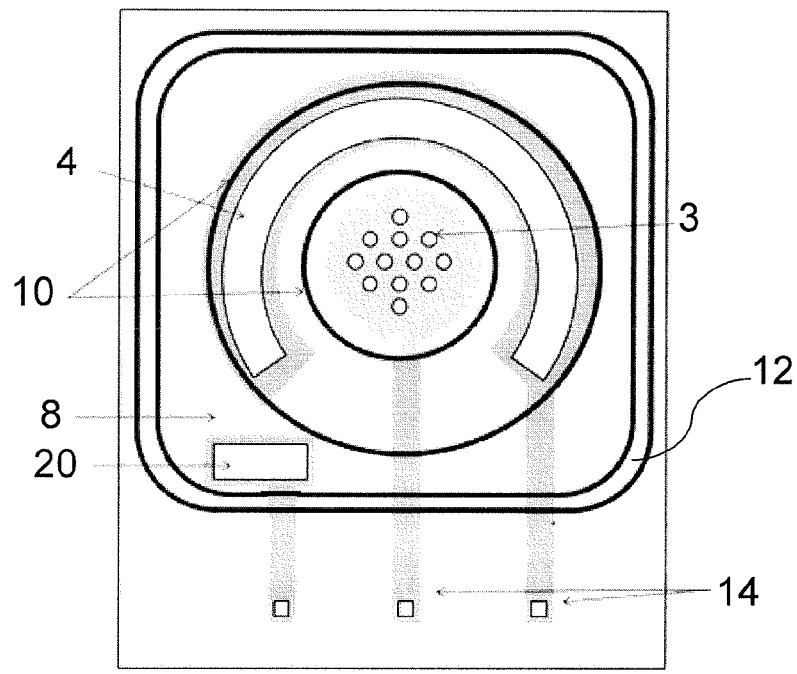
FIG. 3 is a top view of another alternative embodiment of a sensor according to the invention.

The first polymer membrane 10 is preferably formed by a hydrogel, such as a hydrogel preferably made from polyhydroxyethyl-methacrylate (polyHEMA). It is photopolymerized on the silicon wafer with a mask whereof the geometry is defined so that the membrane 10 covers either the openings of the second insulating layer 8 defining the working electrode only, as in the circle shown in FIG. 1, or the working electrode and the counter electrode, or the entire sensor, as shown in FIG. 3.

The first polymer membrane 10 defines the diffusion conditions, and thereby creates a reproducible limit diffusion condition, defined by the thickness of the membrane, making it possible to obtain an amperometric signal that is independent of the flow of the liquid around the sensor, and to protect the electrodes from particle depositions. Thus, the obtained sensor does not require maintenance for one year. If it is changed at the end of a year, the sensor will not have required any intermediate maintenance. The membrane deposited on the electrodes also makes it possible to use a simple potentiostat, since the membrane protects the electrodes from any deposition. The selectivity of the sensor for the oxidation reduction substance is defined by the appropriate potential applied between the reference electrode and the working electrode, as well as by the definition of the polymerization of the membrane.

A second polymer membrane 12 can be deposited above the first polymer membrane 10, with for example a thickness three to six times greater than that of the first polymer membrane 10. Such a second membrane 12 can be made from polysiloxane photopolymerized on the silicon wafer. According to the covered surface, the function of the second membrane 12 is to choose the species to be measured, such as dissolved oxygen, and/or to define the lateral limits of the epoxy resin used for the final encapsulation. The final encapsulation step of the sensor is thus facilitated.

The reference electrode is made by a fine layer of Ag—AgCl on the silicon wafer or by a flat metallic structure connected to the wafer or simply by a wire connected to the wafer and made up of Ag—AgCl, making a pseudo-reference. Very advantageously, the reference electrode is solid, without gel and without liquid, which makes it possible not to have to perform maintenance.

The sensor also comprises openings in the second insulating layer 8 on the chip side, also connected to the electrodes underneath, allowing the electrical contacts 14 of the connecting wires to connect the electrodes to a measuring circuit outside the amperometric sensor. The second insulating layer 8 being arranged on the entire metal layer to make the electrodes, the latter are therefore directly accessible on the sensor side through said layer to produce the electrical contacts.

Figure 4:
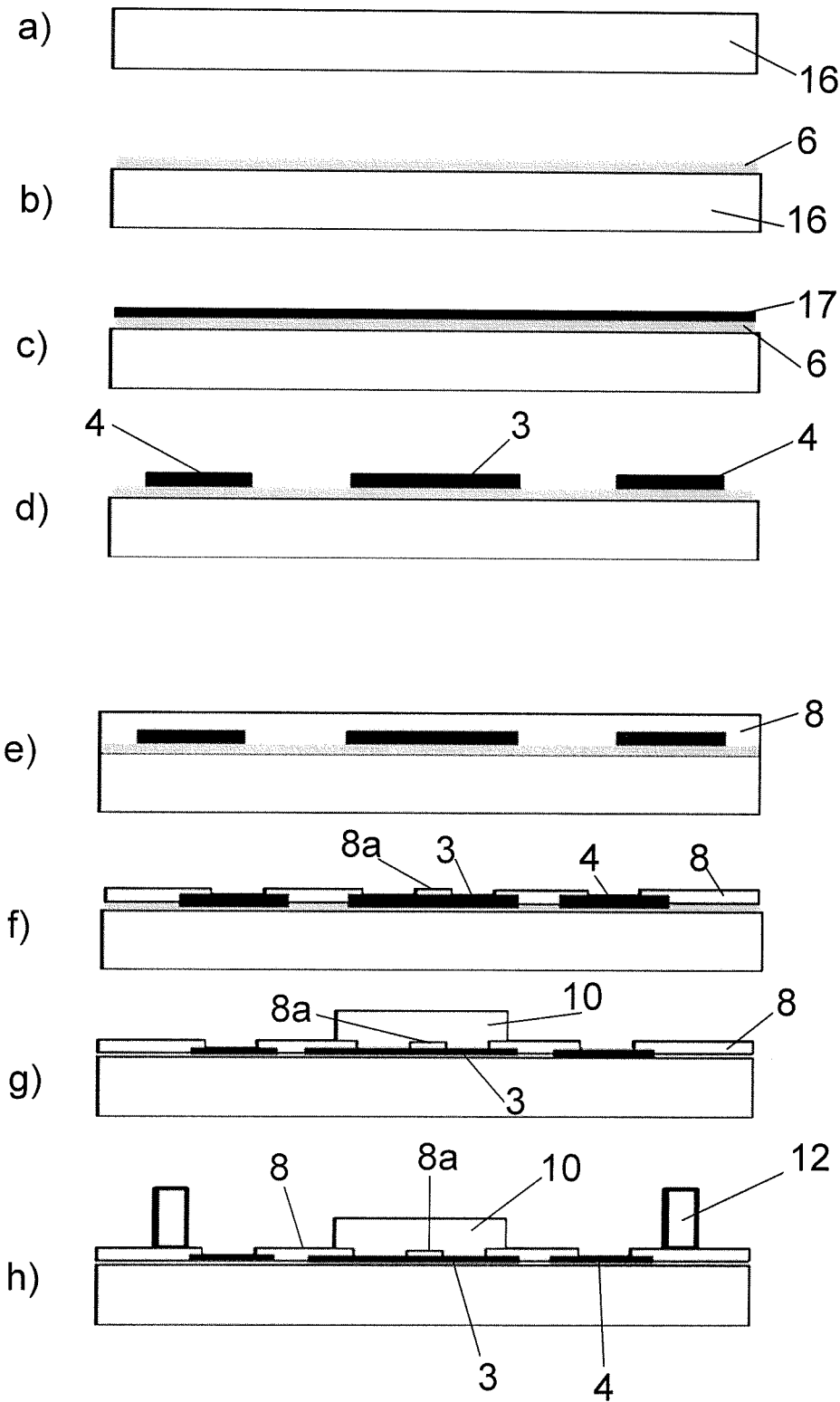
FIG. 4 shows the different steps of a manufacturing method according to the invention.

The sensor according to the invention can be obtained using the method diagrammatically illustrated in FIG. 4. One starts from step a) with a silicon wafer 16. In step b), that wafer is oxidized to form the first insulating layer 6 and therefore form the insulating substrate 2. In step c), a fine layer of metal 17 is deposited on the substrate, in which the working electrode 3 and the counter electrode 4 will be formed. In step d), the metal layer 17 is etched to coarsely define the electrodes 3 and 4. In step e), a second insulating layer 8 is deposited at a low temperature on the metal layer 17. In step f), the openings are formed in the insulating layer 8 to precisely expose the active surface of the working electrode 3 and the counter electrode 4. For example, in FIG. 1, a small island 8a of insulator is kept at the center of the electrode. This small island can be of various sizes, or can be periodically repeated on the surface of the electrode, and have microscopic dimensions, in the vicinity of several micrometers to several tens of micrometers, or nanometric, smaller than a micrometer. Its repetition can be geometric or random, but homogenous on the electrode. To that end, one uses a photolithographic mask and a chemical etching method, which makes it possible to form the working electrode and the counter electrode in a single step having the desired configuration by simply using a mask having the corresponding configuration. The other preceding steps can be shared by all of the sensors, irrespective of the geometry of the electrodes.

In step g), the first polymer membrane 10 of polyHEMA hydrogel is deposited by photopolymerization and using a suitable mask on the openings of the second insulating layer 8 defining the working electrode 3. As seen above, the first membrane 10 defines the diffusion layer and has improved adhesion due to its preferential adhesion to the different elements of the second insulating layer 8.

In step h), the second, polysiloxane-based polymer membrane 12 is deposited by photopolymerization to prepare the encapsulation step of the sensor. Depending on the shape of the photopolymerization mask, this second membrane 12 can also cover the surface of the first polymer membrane 10, and make it possible to impart another selectivity to the sensor.

The inventive sensor can be manufactured using the photolithography methods traditionally used to produce semiconductor components from silicon wafers.

Thus, the advantages of the production of silicon wafers by batches allows excellent reproducibility of the thickness of the membranes, as well as excellent reproducibility of the sensitivity of the obtained wave for the oxidation reduction species. Compared to standard electrodes with reagents, the signal/noise ratio is very high due to the geometry of the well-defined active surface of the electrodes and the well-controlled diffusion layer.

Figure 2:
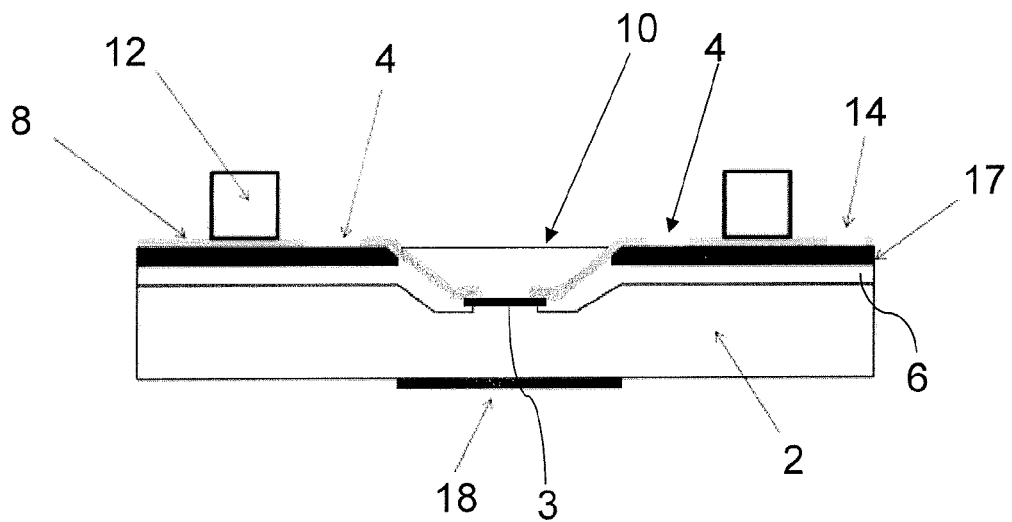
FIG. 2 is a cross-sectional view of another alternative embodiment of a sensor according to the invention.

FIG. 2 shows another alternative embodiment of the inventive sensor. According to this alternative, the substrate 2 has a non-planar structure, for example obtained by anisotropic chemical etching of a p doped conductive silicon. The first insulating layer 6, the metal layer 17 and the second insulating layer 8 are applied as described above. The working electrode 3 and the counter electrode 4 are formed by the openings in the second insulating layer 8. A first poly HEMA hydrogel membrane is applied on the second insulating layer 8 and its opening defining the working electrode 3. A second polysiloxane membrane 12 is deposited to prepare the encapsulation. The electrical contacts 14 are provided as well as rear contacts 18 for the working electrode 3.

The working electrode 3 has been applied following the configuration of the substrate 2, so that it is pushed into the silicon wafer and is thus protected. Furthermore, in that configuration, the contact of the working electrode is achieved by directly using the silicon wafer.

FIG. 3 shows another alternative embodiment of the sensor according to the invention. The references designate the same elements as in the preceding figures. In this alternative, the working electrode 3 is in the form of an array of microelectrodes and elements of the first polymer membrane 10 covering the second insulating layer 8 and the microstructured or nanostructured openings, defining the working electrode 3 and the counter electrode 4. However, this array can be sized in the form of a nanostructure randomly but homogenously distributed over the electrode. The Ag—AgCl reference electrode 20 is integrated into the sensor, and is surrounded by the second polymer membrane 12, allowing its contact with the aqueous medium after encapsulation of the sensor in the resin. The electric contacts are indicated by reference 14.

The sensor according to the invention is used in an amperometric probe to measure the content of an oxidation reduction substance dissolved in a liquid, this dissolved oxidation reduction substance for example being a disinfecting species of said liquid. Particularly advantageously, the sensor is integrated into a detachable dry measuring head, therefore without electrolytes, which can be removably mounted to a probe body, comprising the data processing and transmission means.

Figure 5:
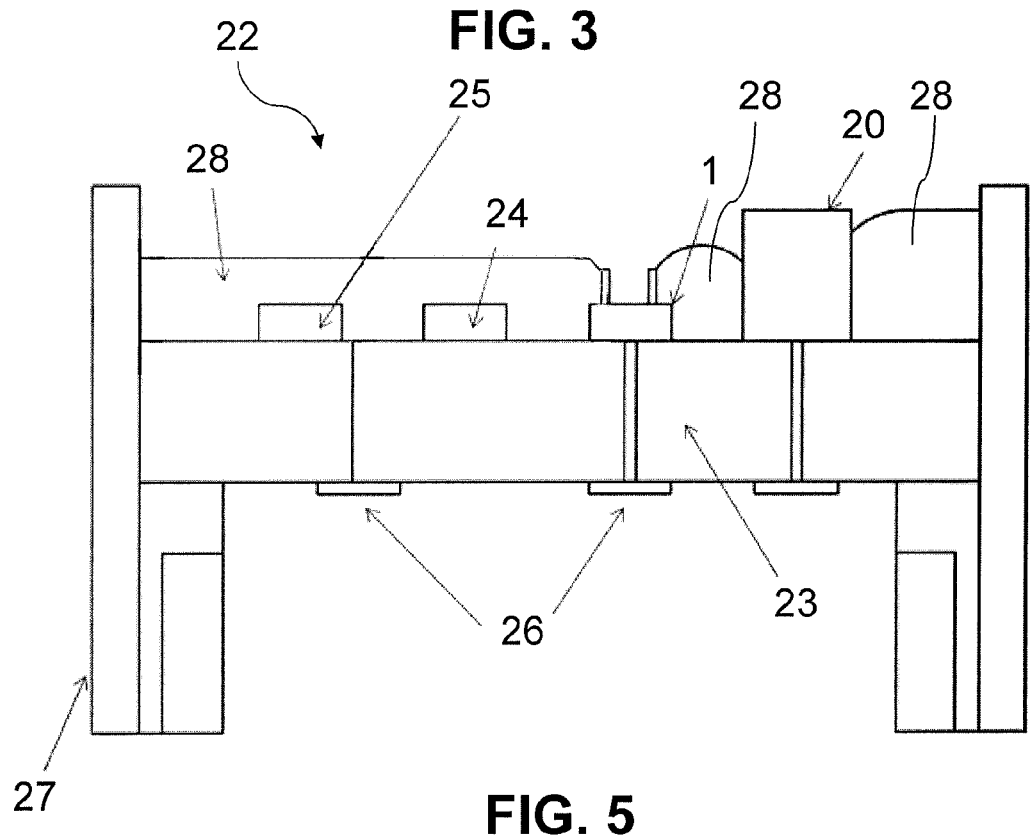
FIG. 5 shows a diagrammatic cross-sectional view of the head of a probe according to the invention.

One such detachable head 22 is shown in FIG. 5. It comprises a printed circuit 23 on which are mounted, on the side opposite the body of the probe, the inventive sensor 1 comprising the working electrode and the counter electrode, the reference electrode, an integrated interface circuit for amplifying and processing the signal 24 to convert the current signal from the sensor 1 into a voltage signal and amplify it, this integrated circuit 24 also being able to measure the temperature, as well as an integrated circuit of the memory type 25. This integrated memory circuit contains the calibration parameters for the detachable head as well as the manufacturing references and a unique identification number. This number can be used to encode the communication with the probe body. Thus, each probe can only operate with one head selection, chosen during manufacture. The rear face of the printed circuit 23 comprises simple contacts 26 to transmit the electric signal coming from the body of the probe, and proportional to the oxidation reduction species to be measured. The printed circuit 23 and all of its components are encapsulated or molded in a plastic housing 27, e.g. PVC, and are covered with a layer of protective polymer resin, for example epoxy 28, leaving the sensor 1 and the reference electrode 20 accessible. The measuring head of the probe 22 therefore does not contain any chemical product or reagent and is therefore biocompatible with water or any other liquid.

The calibration parameters, such as the zero or the sensitivity, and an encoding and identification number can be recorded in the memory circuit 25 of the head during the manufacture thereof. They will then be recovered by the body of the probe for self-calibration.

The measuring head can be easily removed and replaced on site by the user without the assistance of a specialized technician.

Advantageously, two sensors according to the invention can be provided in the measuring head. These sensors are mounted and connected so as to obtain two electronic signals of the species to be measured.

Figure 6:
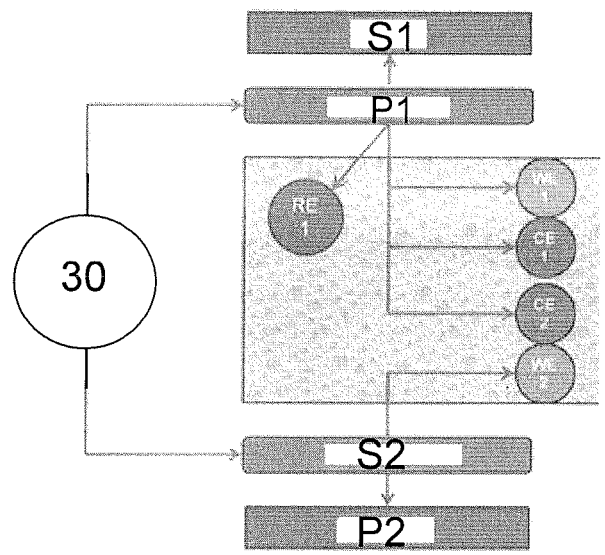
FIG. 6 diagrammatically illustrates the assembly of two sensors used in a same probe head.

The assembly diagram for the two sensors is shown in FIG. 6. The circuit comprises a battery 30, powering a first potentiostat P1 and a second potentiostat P2. The potentiostat P1 is connected to the reference electrode RE1, the working electrode WE1 and the counter electrode CE1 of the first sensor, as well as the counter electrode CE2 of the second sensor. The second potentiostat P2 is connected to the working electrode WE2 of the second sensor. The first potentiostat P1 provides a first signal S1 and the second potentiostat P2 provides a second signal S2. This allows redundancy in the signal with two chlorine signals but a single reference electrode. The processing circuit for the signal can then linearly combine the two signals, by delivering the sum and the difference, so as to obtain an operational status signal of the probe, in particular for the quality of the measurement of the detected electrochemical species. A simple algorithm can be introduced into the probe body software to calculate the quality of the measurement, therefore the aging of the probe, and in particular to transmit an alarm signal if one of the two sensors is defective.

Advantageously, the probe can comprise at least two of the inventive sensors, each comprising a different selective membrane to respectively detect a dissolved oxidation reduction substance different from that of the other sensor.

The housing 27 of the measuring head 22 can comprise a screw pitch cooperating with a corresponding thread provided on the probe body.

Figure 7:
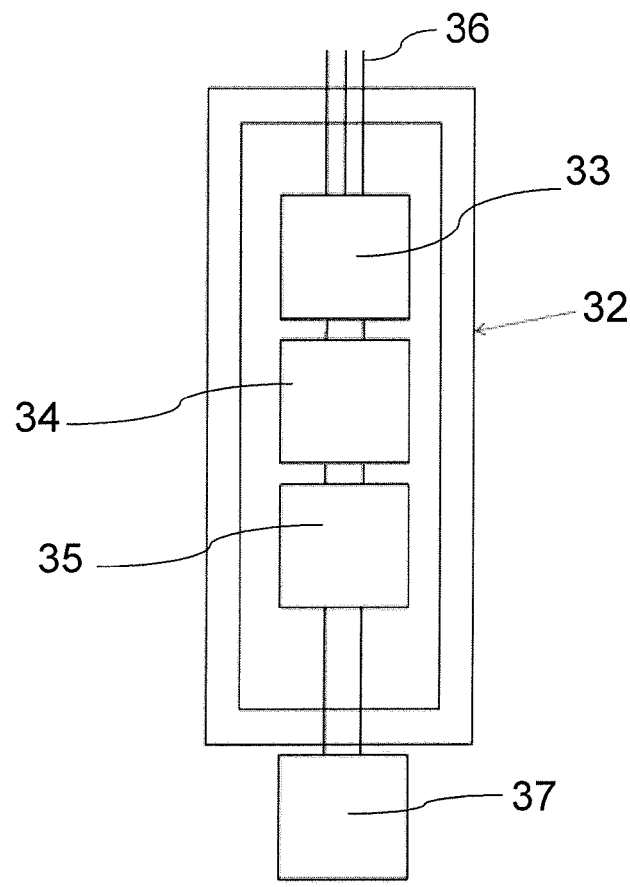
FIG. 7 diagrammatically illustrates the body of a second probe according to the invention, and FIG. 8 diagrammatically illustrates a probe according to the invention.

In reference to FIG. 7, the probe body 32 can be made from plastic or metal. It comprises a printed circuit on which an interface circuit 33, a data decoding and processing circuit 34, such as a microcontroller, and data transmission means 35 in order to transmit the signal representing the content of the measured oxidation reduction species outside the probe are mounted. These transmission means can be a radio system, for example GSM, or an electric cable. The probe body also comprises connection means 36, arranged to connect the printed circuit of the probe body to the contacts 26 provided on the measuring head 22. A battery 37 is also provided, powering the printed circuit of the probe body. These means can also be made by a low-range electromagnetic wave between the measuring head and the probe body.

Figure 8:
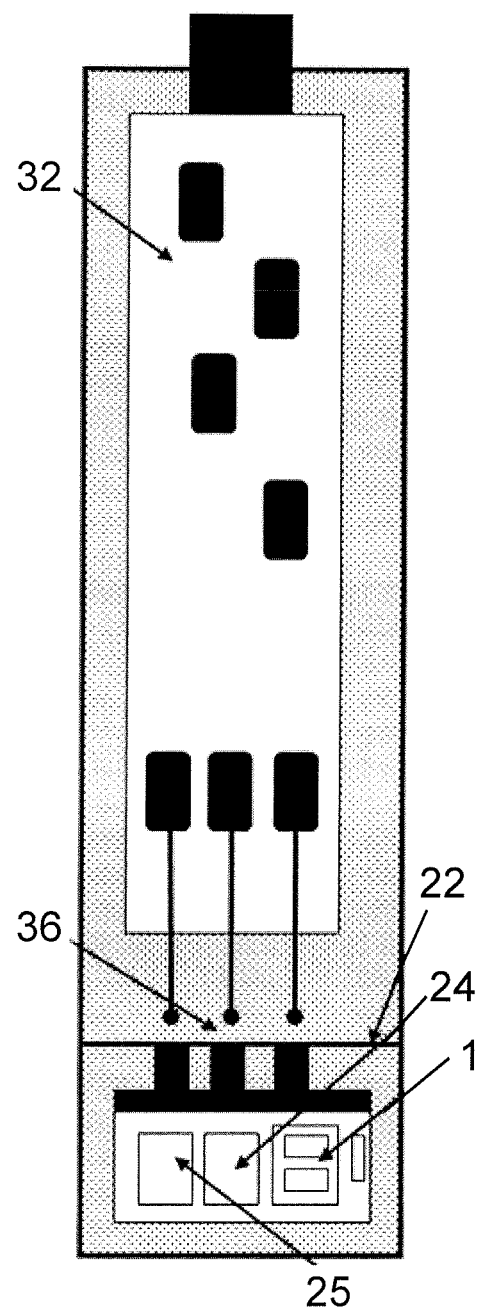

When the measuring head 22 is mounted on the body 32, a measuring probe as shown in FIG. 8 is obtained. When the sensor 1 must be replaced periodically, only the measuring head 22 needs to be changed. The body 32 of the probe that contains the data processing circuit does not need to be replaced.

The obtained probe in particular makes it possible to measure the quality of the water on line, directly in the channels. It has the advantage of withstanding high pressures (10 bars), and of not requiring maintenance. It is easily possible to change only the measuring head comprising the sensor, for example once per year. It does not use chemical reagents to detect the species to be analyzed and is therefore particularly ecological and does not pollute the fluid to be measured, for example potable water.

Of course, in another alternative, the sensor can be integrated into a probe in a single piece.

The invention claimed is:

1. A method for measuring the content of an oxidation reduction substance dissolved in a liquid, comprising the step of: measuring the content of an oxidation reduction substance dissolved in a liquid using, with a fixed potential, at least one amperometric electrochemical sensor comprising an insulating substrate, a set of electrodes, the set of electrodes including a working electrode, a counter electrode and a reference electrode, the working electrode having a top surface with a periphery edge, at least one of said working electrode and counter electrode being located on a top surface of said insulating substrate, and an insulating layer comprising insulating material extending over the top surface of the insulating substrate, the insulating layer covering said working electrode, wherein said insulating layer completely covers the periphery edge of the top surface of said working electrode, wherein said insulating layer comprises plural openings exposing portions of the top surface of said working electrode, said openings being separated by small islands of the insulating material located on the top surface of said working electrode, and wherein the portions of the top surface of the working electrode exposed by said openings and the small islands on the working electrode are completely covered with at least a first polymer filtration membrane, the first polymer filtration membrane having a selectivity to said dissolved oxidation reduction substance to be measured and defining a diffusion layer for said oxidation reduction substance.

2. The method according to claim 1, wherein said oxidation reduction substance is a disinfecting species of said liquid.

3. The method according to claim 2, wherein said liquid is water and the disinfecting oxidation reduction substance is chosen from the group consisting of HOBr, HOCl, $ClO_2$, $Cl_2$, Chloramines and ozone.

4. An amperometric electrochemical sensor with a fixed potential for measuring the content of an oxidation reduction substance dissolved in a liquid, said amperometric electrochemical sensor comprising:
an insulating substrate,
a set of electrodes, the set of electrodes including a working electrode, a counter electrode and a reference electrode, the working electrode having a top surface with a periphery edge,
at least one of said working electrode and counter electrode being located on a top surface of said insulating substrate, and
an insulating layer comprising insulating material extending over the top surface of the insulating subtrate,
the insulating layer covering said working electrode, wherein said insulating layer completely covers the periphery edge of the top surface of said working electrode,
wherein said insulating layer comprises plural openings exposing portions of the top surface of said working electrode, said openings being separated by small islands of the insulating material located on the top surface of said working electrode, and wherein the portions of the top surface of the working electrode exposed by said openings and the small islands on the working electrode are completely covered with at least a first polymer filtration membrane, the first polymer filtration membrane having a selectivity to said dissolved oxidation reduction substance to be measured and defining a diffusion layer for said oxidation reduction substance.

5. The sensor according to claim 4, wherein said counter electrode is covered with said insulating layer, at least one opening of said insulating layer exposing said counter electrode, and wherein the counter electrode exposed by said opening is completely covered by at least said first polymer membrane.

6. The sensor according to claim 4, wherein said first polymer membrane completely covers said opening by overhanging on the insulating layer through its entire peripheral zone.

7. The sensor according to claim 4, wherein the working electrode is non-planar and is arranged in a recess on the top surface of the insulating substrate, said polymer membrane being made so that its upper surface is at the insulating substrate comprising the counter electrode.

8. The sensor according to claim 4, further comprising a second polymer membrane deposited on the first membrane to select the species to be measured.

9. The sensor according to claim 4, wherein the first polymer membrane covers all of the openings.

10. The sensor according to claim 4, wherein the first polymer membrane includes several membrane elements respectively covering each opening by individually overhanging on the insulating layer through their respective peripheral zone.

11. The sensor according to claim 4, wherein the insulating layer comprises homogenous nanostructured openings.

12. The sensor according to claim 4, wherein the substrate is made in a material chosen from among the group consisting of silicon, glass, ceramics and quartz.

13. The sensor according to claim 4, wherein at least one of the working electrode and counter electrode have a shape chosen from the group of a circular, microperforated and interdigitated shape.

14. The sensor according to claim 4, further comprising connection means for connecting the electrodes to a measuring circuit, said connection means being directly connected to the electrodes, the connection means being electrical contacts and wires.

15. An amperometric electrochemical sensor with a fixed potential for measuring the content of an oxidation reduction substance dissolved in a liquid, said amperometric electrochemical sensor comprising:

an insulating substrate having a top surface;
a first insulating layer contactingly covering the top surface of the insulating substrate;
a working electrode located in contact with an upper surface of said first insulating layer;
a counter electrode located in contact with the upper surface of said first insulating layer and spaced apart from said working electrode,
the working electrode and the counter electrode each having a top surface with a periphery edge;
a second insulating layer extending over the top surface of the insulating substrate and completely covering at least the periphery edges of the top surface of said working electrode and said counter electrode,
wherein said second insulating layer comprises plural openings exposing portions of the top surface of said working electrode and said counter electrode, said openings being separated by small islands of the insulating layer located on the top surface of said working electrode and the counter electrode, the openings being microscopic or nanoscopic, and
wherein the portions of the top surface of the working electrode and the counter electrode exposed by said openings define active surfaces of the working electrode and the counter electrode, and at least one of said islands is located on the top surface of, and at a center of, said working electrode; and
a first polymer membrane completely covering the openings located on the top surface of the working electrode, the first polymer membrane extending over and overhanging on an entire peripheral zone of the first insulating layer that covers the periphery edge of the top surface of said working electrode, the first polymer filtration membrane having a selectivity to said dissolved oxidation reduction substance to be measured and defining a diffusion layer for said oxidation reduction substance.

16. The sensor according to claim 15, wherein,
the working electrode is arranged in a recess on the top surface of the insulating substrate at an elevation lower than the counter electrode, and
an upper surface of said first polymer membrane is at a level with the second insulating layer.

17. An amperometric electrochemical sensor with a fixed potential for measuring the content of an oxidation reduction substance dissolved in a liquid, said amperometric electrochemical sensor comprising:

an insulating substrate having a top surface;
a working electrode located over an upper surface of said insulating substrate;
a counter electrode located in contact with the upper surface of said first insulating layer and spaced apart from said working electrode,
the working electrode and the counter electrode each having a top surface with a periphery edge;
an insulating layer extending over the top surface of the insulating substrate and completely covering at least the periphery edge of the top surface of said working electrode,
wherein said insulating layer comprises plural openings exposing portions of the top surface of said working electrode, said openings being separated by small islands of the insulating layer located on the top surface of said working electrode, and
wherein the portions of the top surface of the working electrode exposed by said openings define active surfaces of the working electrode, and at least one of said islands is located on the top surface of said working electrode and spaced apart from the periphery edge of the top surface of said working electrode; and
a first polymer membrane completely covering the openings located on the top surface of the working electrode, the first polymer membrane extending over and overhanging on an entire peripheral zone of the first insulating layer that covers the periphery edge of the top surface of said working electrode, the first polymer filtration membrane having a selectivity to said dissolved oxidation reduction substance to be measured and defining a diffusion layer for said oxidation reduction substance.

18. The sensor according to claim 17, wherein,
the working electrode is arranged in a recess on the top surface of the insulating substrate at an elevation lower than the counter electrode, and
an upper surface of said first polymer membrane is at a level with the second insulating layer so as to fill said recess.

* * * * *